United States Patent
Da Fonseca et al.

(10) Patent No.: US 6,900,290 B2
(45) Date of Patent: May 31, 2005

(54) FRACTIONATION OF WHEY PROTEINS BY COMPLEX FORMATION

(75) Inventors: Leorges M. Da Fonseca, Belo Horizonte-MG (BR); Robert L. Bradley, Jr., Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 473 days.

(21) Appl. No.: 10/095,856

(22) Filed: Mar. 12, 2002

(65) Prior Publication Data

US 2003/0004316 A1 Jan. 2, 2003

Related U.S. Application Data

(60) Provisional application No. 60/277,765, filed on Mar. 20, 2001.

(51) Int. Cl.[7] .................................................. C07K 1/36
(52) U.S. Cl. ...................... 530/366; 530/344; 424/535
(58) Field of Search ........................... 514/8; 424/157.1, 424/535; 426/41; 530/366, 344

(56) References Cited

U.S. PATENT DOCUMENTS

| | | |
|---|---|---|
| 5,756,680 A | 5/1998 | Ahmed et al. |
| 5,925,737 A | 7/1999 | Tomasula et al. |
| 5,986,063 A | 11/1999 | Etzel |

FOREIGN PATENT DOCUMENTS

EP 0 340 035 A2 11/1989

OTHER PUBLICATIONS da Fonseca LM, Bradley RL. Fractionation of whey proteins by complex formation and membrane filtration. University of Wisconsin. Dissertation Abstracts International, (1999) vol. 61, No. 2. Particularly pp. 105–178.*

Eigel et al. (1984) *J. Dairy Sci.* 67:1599–1631.

Fonseca et al. (1999), Fractionation of whey proteins by complex formation (Abstract), *Journal of Dairy Science*, vol. 82, Suppl. 1, p. 27.

Mott et al., (1999), Effect of Xanthan Gum on Enhancing the Foaming Properties of Whey Protein Isolate, *JAOCS*, vol. 76, No. 11, pp. 1383–1386.

Pearce & Kinsella (1978) *J. Agric. Food Chem* 26:716–723.

* cited by examiner

*Primary Examiner*—Bruce R. Campell
*Assistant Examiner*—Andrew D. Kosar
(74) *Attorney, Agent, or Firm*—Joseph T. Leone, Esq.; DeWitt Ross & Stevens S.C.

(57) ABSTRACT

Disclosed is a method of fractionating $\alpha$-lactalbumin from $\beta$-lactoglobulin in whey or whey protein concentrate. The method includes the steps of contacting whey or whey protein concentrate with a complexing agent so that the complexing agent forms insoluble complexes with $\beta$-lactoglobulin present in the whey or whey protein concentrate. The insoluble complexes are then separated from the whey or whey protein concentrate, thus yielding a precipitate that is predominately $\beta$-lactoglobulin and is substantially devoid of $\alpha$-lactalbumin, and a supernatant that predominately $\alpha$-lactalbumin and is substantially devoid of $\beta$-lactoglobulin.

38 Claims, 7 Drawing Sheets

FRACTIONATION OF WHEY PROTEINS BY COMPLEX FORMATION

Priority is hereby claimed to provisional application Ser. No. 60/277,765, filed Mar. 20, 2001, and incorporated herein by reference.

FIELD OF THE INVENTION

The invention is directed to a method of fractionating proteins from whey and whey protein concentrate (WPC) by complexing specific proteins contained in whey with one or more polysaccharide complexing agents. The complexing agent specifically and preferentially forms insoluble complexes with only specific proteins present in the whey, thereby enabling fractionation of the proteins contained therein.

BACKGROUND

Increasing demand worldwide for food production, especially in less developed countries, has sharpened interests in developing alternative sources of nutritionally significant proteins. Simultaneously, awareness has been focused more toward utilizing traditional by-products from the food industry for obtaining these new ingredients. In short, the food industry has, in recent years, focused on utilizing traditional food sources more fully and efficiently.

Whey is an ubiquitous liquid by-product obtained during the cheesemaking process. Raw whey contains highly nutritive proteins, albeit at relatively low concentrations. The high cost of current methods used to isolate these proteins has resulted in whey being a highly-underutilized source of nutritionally significant proteins.

In 1997, the world production of milk was estimated to be 471 million metric tons. Worldwide total production of cheese in 1997 was approximately 13 million metric tons. While no precise figures are available on the quantity of liquid whey produced, based upon the known total output of cheese and casein, an estimated 118 million metric tons of liquid whey was produced worldwide in 1997. This amount of raw liquid whey is equivalent to approximately 7 million metric tons of whey solids. Only about 62% of the worldwide production of whey is utilized for any purpose (food-related or otherwise). The remaining 38% is discarded as waste. In 1995, total whey powder production in the United States was 648,000 metric tons, with a production of 108,000 metric tons of WPC.

Thus, there remains a long felt and unmet need to utilize the nutritive components found in whey. For example, the proteins found in whey can be used as nutritional ingredients in milk that has been altered for infant consumption. These proteins can also be used as dietary supplements and in various food products. For example, whey proteins can be used as functional ingredients in foods, such as in the use of texture or consistency modifiers. emulsifiers, and the like. Whey proteins have excellent functional properties, and the functionality of these various proteins is related directly to their composition. Thus, an efficient and economic method to fractionate whey into its component proteins would result in the more complete utilization of whey as a food source.

A basic requirement for utilizing whey as a source of proteins is a method that isolates the whey proteins in good quality and low cost. For protein utilization in particular, not only must the proteins be isolated with good microbiological properties, but also their physical and chemical qualities must also be preserved. However, for the majority of food applications that would use proteins from whey, it is necessary to obtain these proteins in a more concentrated form. It may also be necessary to separate specific proteins. Several processes are now known for obtaining concentrated proteins or protein fractions from whey. These methods include ultrafiltration, ion exchange, electro dialysis, reverse osmosis, heat precipitation, and precipitation by complexation, among other methods. However, all of these methods entail certain insurmountable barriers, such as economics, time, or ease of use.

At present, the most widely used method of whey protein concentration is via ultrafiltration. Other methods of concentration often require high power energy consumption, have relatively low productivity, result loss of protein functionality as a result of denaturation of the proteins, and sometimes require additional purification steps.

Whey contains water, lactose, proteins, minerals, and residual fat. Lactose is the major component, with only about 6% of the total lactose found in milk being retained in the cheese curd during the cheesemaking process. Whey also has a high mineral content, which can be as much as 70% of the total whey protein weight. Conventionally, whey is used in the manufacture of certain kinds of cheese, such as ricotta. Other conventional uses are field spraying, animal feeding, alcohol production, drying for food use, wine and drink manufacture, and production of other components, such as lactose, yeast biomass, and proteins.

The term whey proteins per se refers to the milk proteins that remain soluble at pH 4.6 and at a temperature of 20° C. See, Eigel et al. (1984) J. Dairy Sci. 67:1599–1631. In the 1950's, the composition of whey was generalized as containing "true protein" and "non-protein nitrogen." See, for example, Lampert, L. M. (1965) *Modern Dairy Products*, Chemical Publishing Company, Inc., New York, N.Y. According to the classical method, the true proteins were divided into "globulins" and "albumins." According to this definition, the "lactalbumin" fraction of the whey contains proteins that are soluble in neutral, one-half saturated ammonium sulphate or saturated magnesium sulphate. Despite the name "lactalbumin," this fraction contains up to 16% β-lactoglobulin. Thus, the use of the term lactalbumin for this purpose is incorrect because the name lactalbumin is related to a specific protein. In the ensuing years, however, new technologies were devised that enabled the fractionation of α-lactalbumin, β-lactoglobulin, lactoferrin, lactoperoxidase, immunoglobulins, and other minor parts from whey. See, for example, Fox, P. F. (1992) *Advanced Dairy Chemistry—Vol. 1: Proteins*, Vol. 1, Elsevier Applied Science, London, England.

Xanthan gum is a high molecular weight polysaccharide produced commercially using the microorganism *xanthomonas campestris* in a controlled fermentation process. At the end of fermentation, the gum is precipitated from the culture medium using isopropyl alcohol, dried, milled, and packaged. The dominant hexose units in the polysaccharide structure are D-glucose and D-mannose, along with D-glucuronic acid. Xanthan gum can be purchased from a number of international suppliers, including Degussa, which sells xanthan gum under the brand names SATIAXANE and ACTIGUM. Jungbunzlauer, of Geneva, Switzerland, also sells xanthan gum in industrial quantities.

Xanthan gum can be dispersed in hot or cold water, resulting in a viscous, non-thixotropic, opalescent solution. The final pH of a xanthan gum solution at approximately 0.1 to 1.0 percent concentration is approximately 6 to 7. An important characteristic of xanthan gum is that it is acid resistant. It can be dispersed directly into acidic solutions, without significant viscosity changes.

Xanthan gum has a molecular weight that is greater than 2 million Daltons. The polymer backbone of xanthan gum consists of 1,4-linked β-D-glucuronic acid, with D-glucose, D-mannose, and D-glucuronic acid residues. Each repeating block in xanthan gum contains 5 sugar units (2 glucose units, 2 mannose units, and 1 glucuronic acid unit). The final viscosity of a xanthan gum solution will depend on the gum concentration. However, high viscosity solutions occur at low xanthan concentration. Xanthan gum solutions are pseudo-plastic (i.e., sheer-thinning), meaning the viscosity of a xanthan gum solution will decrease as the sheer rate is increased. Pseudo-plasticity is an important property for the function of xanthan gum as a food modifier. For example, it allows suspensions and emulsions to be easily poured from a container due to the decreased viscosity caused by the increased sheer forces encountered when the liquid is poured. This decrease in viscosity is instantaneous and reversible. Another interesting aspect of xanthan gum solutions is that they have a practically constant viscosity at extreme temperature ranges (e.g., a 1% xanthan gum solution has an essentially constant viscosity at temperatures ranging anywhere from −18° C. to approximately 79° C.). Viscosity also remains essentially constant between pH 6 and pH 9, with only small changes in viscosity over the pH range from about pH 1 to about pH 11. In short, xanthan gum solutions make excellent food modifiers because of their high viscosity, high degree of pseudo-plasticity, high yield value, and extreme stability to heat and pH variation, in addition to high compatibility with salts, acids, bases, and enzymes.

Sodium carboxymethylcellulose (CMC) is a water soluble, linear, and long chain of polysaccharide having anionic characteristics. It is a chemically-modified natural gum. Cellulose is reacted with sodium hydroxide to yield alkylcellulose. The alkylcellulose is then treated with sodium monochloroacetate, thus resulting in carboxymethylcellulose. Uses for this polysaccharide are extensive, with particular importance in the food industry.

When characterizing CMC, the number of hydroxyl groups on each anhydroglucose unit of the cellulose backbone that is substituted with the carboxymethyl group is referred to as the "degree of substitution" (DS). Because there are three hydroxyl groups in each glucose unit, the maximum theoretical DS is three. In practice, however, this value is much lower. Commercial samples of CMC have DS values ranging from 0.4 to 1.2. Food grade CMC has DS values of approximately 0.9 or lower. The measurement "degree of polymerization" (DP) is related to the number of molecules in the polymer. In short, the greater the DP, the higher is the viscosity of the CMC solution. Food applications of CMC include thickening agents, suspension agents, stabilization agents, gelation agents, and flow modification agents. Perhaps the widest use of CMC is as a stabilizer in the manufacture of frozen dairy desserts such as ice cream, frozen custard, and instant frozen desserts. The CMC gives these products more consistent uniformity, extended shelf life, and improved tolerance to oscillating temperatures. In acidified and neutral milk beverages, CMC is an effective stabilizer, finding use in egg nog, milkshakes, infant formulas, and chocolate milk. It is also used in bakery products to control moisture uptake.

SUMMARY OF THE INVENTION

Whey protein fractionation by precipitation represents an interesting processing alternative for the dairy industry. Although several methods have been developed for protein fractionation, as noted above, the high cost and low yield of these approaches limit their widespread implementation.

The invention is thus directed to a method that efficiently and cost-effectively separates desirable proteins from whey and whey protein concentrate (WPC) by complexing certain proteins contained in whey with polysaccharide complexing agents under conditions wherein the complexing agent complexes specifically and preferentially with only certain proteins, thereby enabling fractionation of the proteins contained in whey. The preferred complexing agent is xanthan gum.

More specifically, the invention is directed to a method of fractionating whey and WPC which allows rapid and cost-effective isolation of α-lactalbumin and β-lactoglobulin. The method yields α-lactalbumin which is at least 95% pure, and, most preferably, yields α-lactalbumin which is substantially free of β-lactoglobulin and other proteinaceous contaminants. Likewise, the method yields a β-lactoglobulin fraction that is essentially free of α-lactalbumin, and has only small amount of other, minor proteins.

In the preferred embodiment, whey or WPC is treated with xanthan gum under controlled ratios of whey/WPC-to-xanthan gum, temperature, pH, and ionic strength. Under these conditions, described in full hereinbelow, β-lactoglobulin, globulins, and other proteins (with the exception of α-lactalbumin) contained in the whey or WPC will preferentially form complexes with the complexing agent. These complexes form a precipitate which can be physically separated (by any means now know or developed in the future) from the supernatant. The supernatant thus contains substantially pure α-lactalbumin, which is then isolated from the supernatant by means known to the art. The precipitate can also be processed further to yield a dry powder comprising, in major part, β-lactoglobulin.

In general, the process proceeds as follows: filtered and dialyzed whey or WPC is treated with a solution containing apolysaccharide complexing agent under conditions wherein the β-lactoglobulins contained in the whey/WPC complexes with the complexing agent to form insoluble complexes. Under these same conditions, α-lactalbumin present in the whey/WPC remains in the supernatant. The polysaccharide complexing agent is selected from the group consisting of pectin, sodium alginate, propylene glycol alginate, carboxymethylcellulose (low- or high-viscosity), and xanthan gum. Xanthan gum The supernatant is then treated, as by ultrafiltration, to isolate the α-lactalbumin contained therein. The α-lactalbumin so isolated has a purity of at least 95% and often greater than 99% purity.

The precipitate can be treated with an alcohol, preferably isopropanol, to separate the complexes in their component xanthan gum and β-lactoglobulin components. The xanthan gum can be recycled for use in another cycle of the present method. Treatment with an alcohol not only causes disassociation of the complexes, it also renders the xanthan gum insoluble, thereby facilitating isolation of the β-lactoglobulin and proteins which precipitated from the whey/WPC starting material in the form of insoluble complexes.

Thus, the invention is directed to a method of fractionating α-lactalbumin from β-lactoglobulin in whey or whey protein concentrate. The method comprises first contacting whey or whey protein concentrate with a complexing agent under conditions wherein the complexing agent forms insoluble complexes with β-lactoglobulin present in the whey or whey protein concentrate. The insoluble complexes are then separated from the whey or whey protein concentrate, thereby yielding a precipitate that comprises β-lactoglobulin (and that is substantially devoid of α-lactalbumin), and a supernatant that comprises α-lactalbumin (and that is substantially devoid of β-lactoglobulin).

The complexing agents used in the method are preferably selected from the group consisting of pectin, sodium alginate, propylene glycol alginate, carboxymethylcellulose, and xanthan gum. The most preferred complexing agent is xanthan gum.

Optionally, the method may further comprise a step of concentrating the α-lactalbumin present in the supernatant. The method may optionally further comprise the step of disassociating the insoluble complexes contained within the precipitate and isolating β-lactoglobulin from the disassociated complexes. The complexing agent from the disassociated complexes may also be recovered and used again.

It is preferred that the precipitate be treated with an alcohol to disassociate the complexes, preferably a C1 to C6 alcohol, and most preferably isopropyl alcohol.

In the preferred embodiment, the whey or whey protein concentrate is contacted with the complexing agent in an aqueous solution of about pH 4.0, and having an ionic strength of from about 0.01 to about 0.50. It is also preferred that the whey or whey protein concentrate comprises an aqueous solution containing no less than about 0.20% wt/vol whey proteins and that the complexing agent comprises an aqueous solution containing no less than about 0.05% wt/vol of the complexing agent.

The primary advantage of the invention is that it provides an economical and highly effective means for isolating α-lactalbumin, a desirable protein which could find use in many food and pharmaceutical applications. Presently, isolated α-lactalbumin is not used on an industrial scale due to the cost of isolation and the availability of substitutes (egg albumin). Another advantage of the present invention is that it also provides for a cheap and highly effective means for isolating β-lactoglobulin and immunoglobulins from whey. Both advantages are beneficial to cheese makers, who normally discard a large portion of the whey generated in the process of cheesemaking.

DETAILED DESCRIPTION OF THE INVENTION

Figure 1:
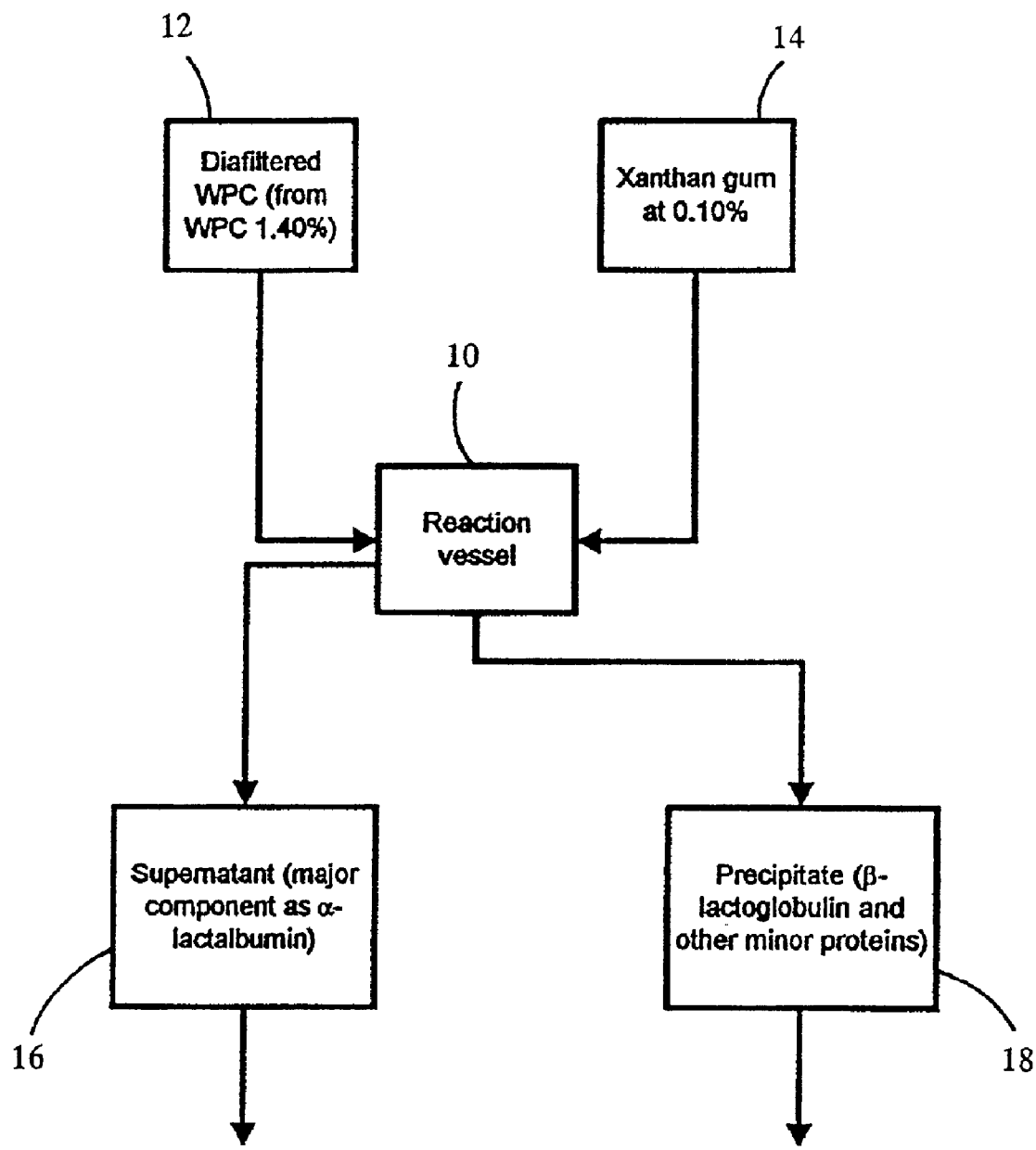
FIG. 1 is a flowchart illustrating the selective precipitation of β-lactoglobulin from whey or WPC according to the present invention.
Figure 2:
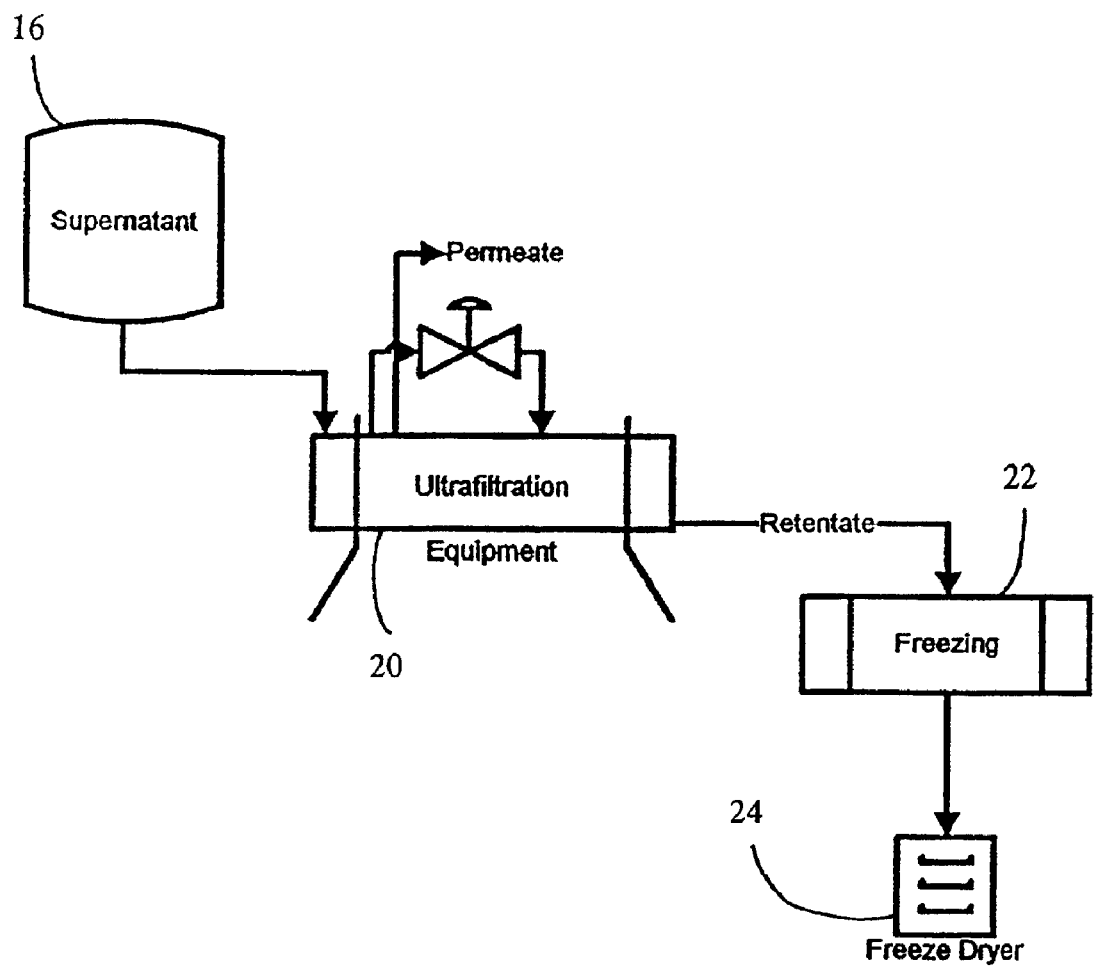
FIG. 2 is a flowchart illustrating the processing of the supernatant from FIG. 1.
Figure 3:
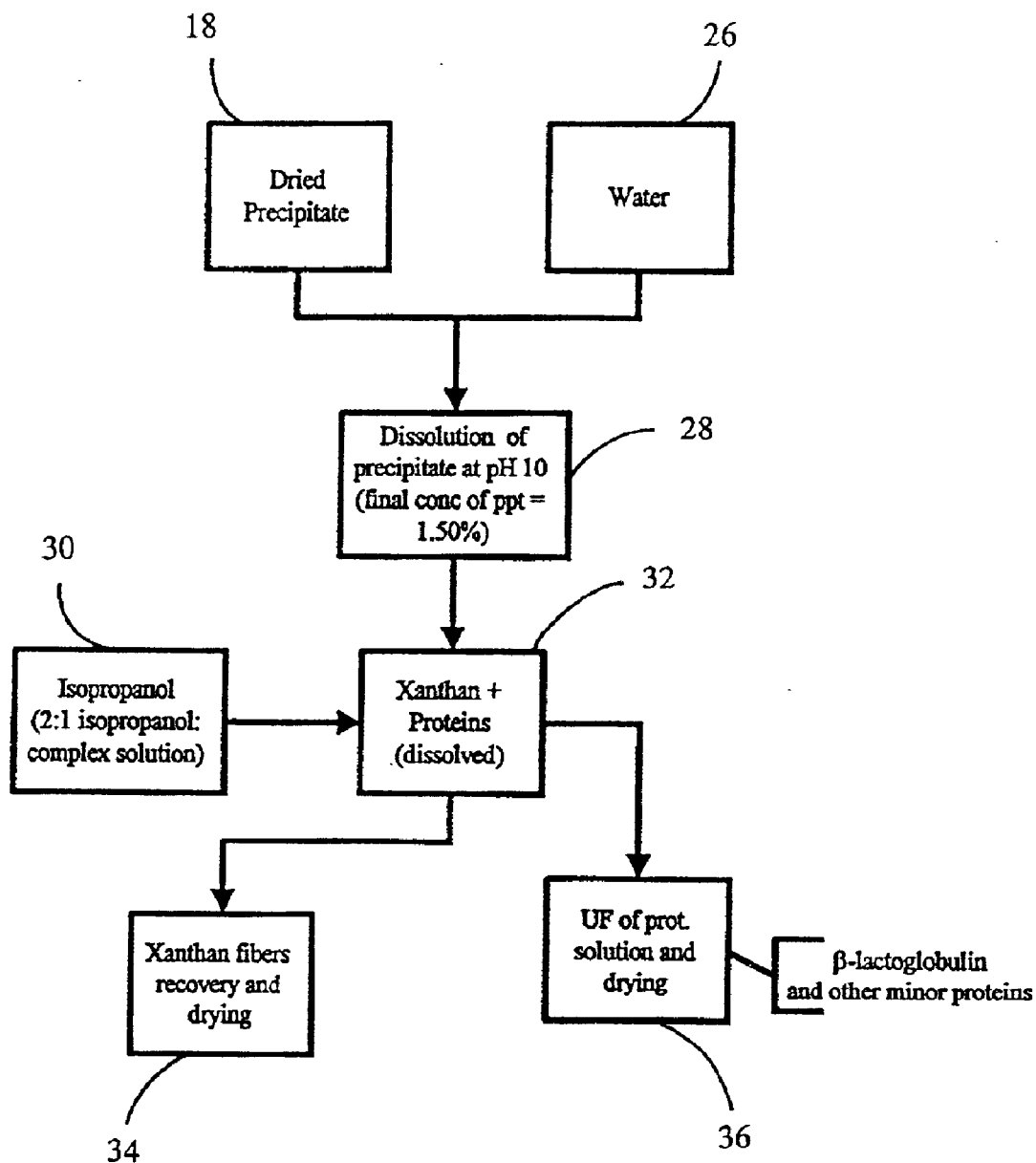
FIG. 3 is a flowchart illustrating the processing of the precipitate from FIG. 1.

Referring now to FIGS. 1, 2, and 3, these figures depict a flow chart of the preferred embodiment of the present invention. In FIG. 1, diafiltered WPC 12 (obtained from reconstituted WPC, 1.40% wt/vol) is introduced into a reaction vessel 10 along with a 0.10% wt/vol solution of xanthan gum 14. The nature of the reaction vessel 10 is not critical to the function of the invention. Any vessel of suitable dimensions will suffice. Preferred, however, is a temperature-controlled vessel, such as a water-jacketed reaction vessel.

As noted hereinabove, the complexing reagent is selected from the group consisting of pectin, sodium alginate, propylene glycol alginate, carboxymethylcellulose, and xanthan gum. For the sake of expository brevity, the following discussion refers solely to xanthan gum, the preferred complexing agent. This is for sake of brevity and clarity only. The invention also functions using any of the other listed complexing agents.

The WPC solution 12 and the xanthan gum solution 14 are preferably added to the reaction vessel 10 in amounts so as to yield a final ratio of protein plus non-protein nitrogen in the WPC to complexing agent (i.e., {protein +NPN in WPC}:complexing agent) of from about 1 to 1 to about 16 to 1. Ratios outside this range are encompassed explicitly by the present invention. The stated range of from about 1 to 1 to about 16 to 1 is simply the preferred range.

The solution is then allowed to reaction within the vessel 10 for a sufficient amount of time to allow for the formation of insoluble complexes. Reaction times can vary anywhere from minutes to hours, although, for economic reasons, it is preferred that the reaction times be as short as possible consistent with maximum complexation of the proteins found in the whey. See the Examples, below, for further discussion.

After the reaction is complete, the supernatant and the precipitate present in the reaction vessel are separated from one another. This can be done using any means for separation now known in the art or developed in the future. The means for separation are not critical to the outcome of the method, so long as the chosen method cleanly separates the supernatant from the precipitate. Thus, suitable means for separation that can be used in the present invention include centrifugation, filtration, microfiltration, ultrafiltration, dialysis, electro dialysis, and the like. Ultrafiltration is the preferred means for separating the supernatant from the precipitate.

Separation yields a supernatant 16 that is highly enriched in α-lactalbumin and substantially devoid of β-lactoglobulin, and a precipitate 18 that is highly enriched in β-lactoglobulin and other proteins and that is substantially devoid of α-lactalbumin. The supernatant can be further processed as shown in FIG. 2. The precipitate can be further processed as shown in FIG. 3.

Referring now to FIG. 2, the supernatant 16, which contains essentially pure α-lactalbumin, uncontaminated by other whey proteins, can be concentrated or all of the moisture removed to yield powdered α-lactalbumin. As shown in FIG. 2, the supernatant 16 is passed through an ultrafiltration unit 20 to isolate the α-lactalbumin contained within the supernatant. The ultrafiltration unit 20 is just one means for separation/isolation that can be utilized to concentration the α-lactalbumin from the supernatant. Other means, such as centrifugation, and the like, may also be used. Ultrafiltration is preferred.

As shown in FIG. 2, the ultrafiltration unit 20 yields a permeate (consisting essentially of water) and a retentate that is very highly enriched α-lactalbumin. The retentate may then be frozen in freezer 22 and lyophilized in freeze dryer 24, thus yielding freeze-dried α-lactalbumin.

Referring now to FIG. 3, the precipitate 18 may be further processed as follows. The precipitate is dried and then mixed with water 26. Preferably, the dried precipitate is mixed with water in a solution that is adjusted to contain 1.5% wt/vol. of the dried precipitate, and the pH of the solution is adjusted (by addition of a base, preferably NaOH) to be about 10. See reference numeral 28. This treatment serves to reconstitute the dried precipitate and to disassociate the xanthan gum from the whey proteins.

To separate the disassociated xanthan gum from the WPC proteins, an alcohol, preferably a $C_1$ to $C_6$ alcohol, and most preferably isopropyl alcohol 30 is added to the dissolved precipitate. This yields a solution 32 containing dissolved WPC proteins and xantban gum, which precipitates from the solution. The precipitated xanthan gum 34 can be separated from the supernatant by any means now known or developed in the future for separating a precipitate from a supernatant (centrifugation, filtration, dialysis, etc). Filtration is preferred. The supernatant 36 contains dissolved protein consisting essentially of β-lactoglobulin that is substantially devoid of α-lactalbumin.

Various embodiments and permutations of the above-described method are illustrated in the following Examples.

EXAMPLES

The following Examples are included solely to provide a more clear and consistent understanding of the invention disclosed and claimed herein. The Examples do not limit the scope of the claimed invention in any fashion.

In all of the Examples that follow, the following materials and methods were utilized.

Reactants

DARITEK® 50-brand whey protein concentrate (WPC) (Foremost, Baraboo, Wis.) was used for all Examples. This WPC is approximately 50% concentrated as compared to raw whey. The WPC was reconstituted with deionized water to a final concentration of about 20% wt/vol. This reconstituted lot was used in bulk for further dilutions. After reconstitution, the samples were stored at 0 to 40° C. To obtain dialyzed WPC, reconstituted 10% wt/vol WPC was dialyzed against distilled water to about 10% of its initial ionic strength. The dialysis tubing used was SPECTRA POR® 1-brand membrane having a nominal molecular weight cut-off of 6000–8000. Conductivity was monitored using a conductivity bridge Model 31A, Yellow Springs Instrument Co., Yellow Springs, Ohio. In Example 4, DARITEK®-brand WPC with 35% protein in dry matter was used.

The gums utilized were diluted with deionized water to reach the desired concentration. After dilution, the samples were stored at 0 to 4° C. The following gums were used: xanthan (Continental Colloids, Chicago, Ill.), sodium carboxymethylcellulose (CMC) (high viscosity), sodium CMC (low viscosity) (Continental Colloids), pectin (Danisco, New Century, Kans.), sodium alginate (Kelco, Chicago, Ill.), and propylene glycol alginate (PGA) (Kelco).

Reaction Conditions

For Example 1 (stoichiometry), reconstituted WPC at 20% wt/vol concentration in distilled water was mixed with 0.20% wt/vol aqueous polysaccharide solution, with the final volume containing apolysaccharide concentration of 0.05% (pectin, alginate, PGA, CMC low viscosity, CMC high viscosity, or xanthan gum) or 0.10% (CMC low viscosity, CMC high viscosity, or xanthan gum). The WPC was added to a final WPC concentration of 0.20, 0.40, 0.60, 0.80, 1.00, 1.20, 1.40, 1.60, 1.80 or 2.00% wt/vol. After WPC addition, the pH was adjusted to 4.0. The reaction proceeded for 15 minutes and then a 50-ml aliquot was collected and centrifuged at 1200× g for 25 minutes. The supernatant was assayed for protein and non-protein nitrogen by the Kjeldahl method and the proteins precipitated by SDS-PAGE. In the second Example, the supernatant after CMC reaction with WPC (final WPC concentration of 0.20% wt/vol) was used for gel permeation chromatographic analysis.

For Example 3 (xanthan gum reaction with WPC containing different ionic strength), 100 ml of xanthan solution at 0.10% wt/vol was reacted with 100 ml of dialyzed 1.40% WPC. Sodium chloride and calcium chloride were added to the dialyzed WPC before reaction to increase ionic strength by 0.01, 0.05, 0.10 and 0.50. The reactions were performed in a double-walled reaction vessel. For maintenance of a constant temperature, water from a temperature-controlled water bath set at 20° C. or at 45° C. was circulated between the walls of the reaction vessel, using a peristaltic pump. Agitation of the reactants in the reaction vessel was by a magnetic agitator and the reaction proceeded for a 15-minute period. After the reaction, 20-ml aliquots of the supernatant were centrifuged at 20° C. and 45° C. and the supernatants assayed for protein content by Kjeldahl analysis and by SDS-PAGE.

For Example 4, samples of 2.00%, 1.00% and 0.50% reconstituted WPC were heated indirectly in a water bath to 90° C. and held for 30 minutes at this temperature, and at 121° C. for 15 minutes in an autoclave. After heating, 50-ml samples of non-heated and heated WPC were reacted with 50-ml 0.20%, 0.10%, and 0.02% xanthan gum solutions and the supernatants were assayed for protein content by Kjeldahl analysis and by SDS-PAGE. The extent of denaturation was measured by the Harlan-Ashworth test (5).

pH

The pH adjustments of WPC and gum solutions were accomplished by adding 1.0 N NaOH or 1.0 N HCl slowly with stirring until the final pH was reached. An ACCUMET®-brand model 15 pH meter (Fisher Scientific) or a CORNING®-brand model 345 pH meter was used after standardization at pH 4.0, pH 7.0, and pH 10.0. pH calibration of the meter was confirmed after every 10 readings.

Centrifugation Equipment and Procedures

The samples were centrifuged for 25 minutes at room temperature using an INTERNATIONALS®-brand centrifuge, size 2, model K (Boston, Mass.), with the operating conditions set to yield 1200× g.

In Example 3, 20-ml aliquots of the supernatant samples were centrifuged at 20° C. and at 45° C. using a METPATH®-brand model OCT-VI centrifuge (Patel Scientific Inc., Paterson, N.J.) at a speed setting of 25. Centrifugation was performed in a temperature-controlled environment. Specifically, the centrifuge was placed inside an incubator and allowed equilibrate for 2 hours before centrifugation. The temperature during centrifugation was monitored by a thermocouple inside the centrifuge.

Compositional Analysis

Moisture was determined using the Association of Official Analytical Chemists (AOAC) method for dried milk. See: Association of Official Analytical Chemists (1990) "Official Methods of Analysis," Fifteenth Ed., Arlington, Va. Samples (1 to 1.5 g) were weighed in a round flat-bottom metal dish, and dried to constant weight in a vacuum oven at 100° C. for 5 hours. Pressure was maintained at about 90 mm of Hg. After drying, samples were removed from oven, cooled in desiccator, and weighed. (See AOAC Method 927.05).

Fat analyses were done using the Mojonnier method (AOAC Method 989.05). A reagent blank was used.

Ash was measured by taking a sample of approximately 1 g of WPC and ashing it at 550° C. in a FUMATROL 1®-brand muffle furnace (Themolyne Corporation-Dubuque, Iowa) for 18 hours. After ashing, samples were transferred to a desiccator to reach ambient temperature prior to weighing each sample (AOAC Method 930.30).

Measurement of total protein was by the Kjeldahl method (AOAC Method 960.52), using a nitrogen conversion factor of 6.38. Non-protein nitrogen was determined using trichloroacetic acid (TCA). Non-protein nitrogen was analyzed as the nitrogen that remained soluble in TCA at concentration of 12% (AOAC Method 991.22). True protein was estimated as the total protein subtracted from non-protein nitrogen converted with the factor 6.38. The procedure was performed in duplicate for each sample.

Lactose was obtained by subtracting the weight of the ash, fat, protein, and moisture of each sample from the total weight of each sample.

Sodium Dodecyl Sulfate-polyacrylamide Gel Electrophoresis (SDS-PAGE)

SDS-PAGE was done using 12.0% T and 2.7% C resolving gels (where % T is the percentage of acrylamide and bisacrylamide and % C is the percentage of bisacrylamide divided by % T). The stacking gels were 4.0% T and 2.7% C in composition. (See Deutscher, M. P. (1990) "Guide to Protein Purification," vol. 182, Academic Press, California.)

The electrophoresis procedure was as follows:

Stock Solutions

Solution 1: Acrylamide concentrate (30.0% T, 2.7% C): contained 29.2 g of acrylamide and 0.8 g of bisacrylamide in 70 ml of deionized water. Volume was made to 100 ml with deionized water and vacuum filtered through a 0.45 $\mu$m pore diameter membrane. The solution was stored at 4° C. in a dark bottle (maximum 1 month).

Solution 2: Tris-Cl, 1.5 M, pH 8.8 concentrated resolving gel buffer: contained 18.2 g of Tris in 80 ml of deionized water, pH was adjusted to 8.8 with HCl, and distilled water added to final volume of 100 ml. This solution was stored at 4° C.

Solution 3: Tris-Cl, 0.5 M, pH 6.8 concentrated stacking gel buffer: contained 6.1 g of Tris added to approximately 80 ml of water, pH was adjusted to pH 6.8 using HCl and volume made to 100 ml. This solution was stored at 4° C.

Solution 4: 10% (wt/vol) sodium dodecyl sulfate (SDS).

Solution 5: Stock sample buffer (0.06 M Tris-Cl, pH 6.8, 2.0% SDS, 10.0% glycerol, 0.025% bromophenol blue): contained 4.8 ml of deionized water, plus 1.2 ml of 0.5M Tris-Cl, pH 6.8 (solution 3), 2.0 ml of 10% SDS (solution 4), 1.0 ml of glycerol, and 0.5 ml of 0.5% bromophenol blue (wt/vol with water). Stored at room temperature.

Solution 6: SDS-reducing buffer: contained 50 $\mu$l of 2-mercaptoethanol added to 0.95 ml of stock sample buffer (solution 5). Solutions were assembled just prior to use.

Solution 7: Catalyst, 10% ammonium persulfate (APS): contained 100 mg of APS in 1 ml of deionized water (prepared daily).

Solution 8: N,N,N,N-Tetramethylethylenediamine (TEMED), undiluted.

Solution 9: Electrode buffer (0.025 M Tris, 0.192 M glycine, 0.1% w/v SDS, pH 8.3): Electrode buffer was made as a 5× concentrate comprising 15 g Tris base, 72 g glycine, and 5 g SDS/liter. The 5× stock solution was stored in glass containers. Prior to use, the 5× concentrate was diluted with four parts of water to yield a final volume of 5,000 ml. The pH was not adjusted at this point, but rather after all reagents were mixed together. The pH of the solutions were then confirmed (pH should be near 8.3±0.2).

General procedure: Casting for four gels required 26.8 ml of water mixed with 20 ml of solution 2, 0.8 ml of solution 4, and 32 ml of solution 1. The mix was deaerated under vacuum for 15 min. After deaeration, 400 $\mu$l of solution 7 and 40 $\mu$l of TEMED (solution 8) were added and the solution mixed gently. The mounted plates were filled using a pipet. Immediately after gel pouring, the gel solutions were covered with a solution of water-saturated 2-butanol to exclude air. Polymerization lasted 90 min. The stacking gels (4.0% T, 2.7% C) were prepared while the resolving gels were polymerizing.

For four stacking gels, 24.4 ml of water was mixed with 10 ml of solution 3, 0.4 ml of solution 4, and 5.2 ml of solution 1. After deaeration under vacuum for 15 minutes, and when the resolving gel was ready and dry, 200 $\mu$l of solution 7 and 40 $\mu$l of TEMED (solution 8) were added to the stacking gel solution and gently mixed. After polymerization of the resolving gel, the top of each gel was rinsed with deionized water and the area of the plates above was dried with filter paper. The stacking gels were allowed to polymerize for 60–90 minutes. When necessary, the resolving gels were allowed to stand overnight before use, and were covered with resolving gel buffer to avoid dehydration and ion depletion.

Sample preparation: To 160 $\mu$l of SDS reducing buffer (525 $\mu$l of 2-mercaptoethanol added to 10.0 ml of stock sample buffer) in micro centrifuge tube was added 40 $\mu$l of supernatant sample (or solubilized precipitate). The solution was then mixed and heated at 95° C. for at least 5 minutes. Aliquots of these samples were loaded in each lane of the gel. For semi-quantitative determination, each gel was loaded with standard samples from a commercial kit (MW-SDS-7OL from Sigma, St. Louis, Mo.). The molecular weight marker was analyzed for protein composition using the Kjeldahl method to obtain the desired concentration of the markers to allow quantitative determination of the protein bands. In addition to this marker, some gels were also loaded with markers containing $\alpha$-lactalbumin, $\beta$-lactoglobulin, and immunoglobulin G (Sigma), or with reconstituted WPC corresponding to the dilution used in the reaction with gums.

The gels were run at 25–30 mA/gel (usually 120 mA/4 gels), with cooled water circulating through the electrode buffer.

Staining & Destaining:

1. Fixative solution (10 hours): contained 40% methanol vol/vol, 10% TCA wt/vol, and 50% water.

2. Staining solution (3 hours): contained 0.2% coomassie brilliant blue R250 in a solution of 30% isopropanol (vol/vol), 10% glacial acetic acid (vol/vol) and 60% water.

3. Destaining solution (15 hours minimum; 25 hours maximum): contained 15% isopropanol (vol/vol), 5% glacial acetic acid (vol/vol), and 80% water.

Image Analysis

After destaining, gels were processed as follows: Gel images were captured using a JVC camera, model 9400 with light filter connected to a PC-computer through a video card with video input. The gel transillumination was done using a light box from a gel reader. The images so collected were further processed using SCION IMAGE®-brand software (from Scion Corporation, Frederick, Md., based on the NIH-IMAGE®-brand software for Macintosh from the National Institutes of Health, Washington, D.C.) running on the WINDOWS®-brand operating system. Calibration was done busing Rodbard calibration. (See software manual, "Scion Image for Windows," 1998.)

Denaturation Measurement

The method utilized was the Harlan-Ashworth assay with slight modifications. Briefly, 20 ml of reconstituted samples were saturated with salt at room temperature and placed in a water bath at 370° C. for 30 minutes. During the first 15 minutes, the tubes were shaken at intervals of 1.5 minutes to assure saturation of the solution. In the remaining 15 minutes, the samples remained undisturbed. Without cooling, the mixture was shaken, and filtered through Whatman No. 42 paper. Every sample was again filtered, then a 5 ml aliquot of filtrate was collected, from which 1 ml was added to a tube. Then 10 ml of saturated sodium chloride was added, the tube stoppered, and the contents mixed slowly by inversion. Two drops of 10% HCl were added to the mixture to develop turbidity. The tube was stoppered again and inverted twice for mixing. Within 5 minutes the tubes were inverted again and the turbidity measured in a spectrophotometer set at 420 nm using a flow-through cuvette (4053 KINETICS®-brand Spectrophotometer, Ultrospec K LKB, Biochrom, Cambridge, England). The spectrophotometer was adjusted to 100% transmission with a casein-free filtrate made from 1 ml of the initial filtrate added to 10 ml saturated sodium chloride solution. Determinations were made in quadruplicate samples and results reported as the average milligrams of undenatured whey protein nitrogen (UWP-N) per gram of WPC, based on a standard curve. In the reconstituted samples of WPC, the results were adjusted to show the equivalent dry weight of WPC.

A standard curve was prepared using 20 g of standard high heat and low heat nonfat dry milk (American Dairy Products Institute, Chicago, Ill.), in 200 ml of distilled water, and 80 g of sodium chloride. Shaking was for 1 minute before putting the sample in the water bath. Exactly 100 ml of each filtrate was collected and 6 samples with different proportions of low heat and high heat standards were prepared. After adjustment of the spectrophotometer for 100% transmittance, the solutions were assayed for % T and a standard curve was plotted with transmittance in the Y-axis and milligrams of UWP-N in the X-axis (% N×factor 6.38).

Gel Permeation Chromatography

After reaction of 0.05% CMC and 0.20% WPC, the mixture was centrifuged, the supernatant fraction was collected, and a gel filtration analysis of the fraction was done (gel permeation column from Pharmacia, Upsala, Sweden). The separating medium in the column was Sephadex G-200 (Pharmacia Fine Chemicals Inc., Piscataway, N.J.) and elution profiles were measured against a commercially-available mixture of standards: SIGMA®-brand MW-GF 1000 (carbonic anhydrase, albumin bovine, alcohol dehydrogenase, β-amylase, apoferritin, and thyroglobulin as standards). The fractions were collected and absorbance was assayed at 280 nm in a spectrophotometer. The column void volume was determined using blue dextran.

Statistical Analysis

Results in each experiment were analyzed using a general factorial analysis of variance, with a least significant difference (LSD) test and accepted significance level of $P<0.05$. For Example 3, statistical analysis involved three fixed factors and a full factorial model. In addition, a one-way analysis of variance between groups test (ANOVA) for each of the treatments combination was done in Example 3 and LSD estimated. For Example 4, a one-way ANOVA was done in each one of the treatment combinations to evaluate the effect of protein denaturation by heating. The software utilized was the MINITAB®-brand statistical software (release 12 for Windows) and SIGMAPLOT®-brand software (See Training Manual "SigmanPlot for Windows", version 5, SPSS Inc., Chicago, Ill.).

Example 1

Determination of Stoichiometric Values for Precipitation of Proteins by Complexation This Example determined, using an aqueous gum solution at fixed concentration, the maximum whey protein precipitation that could be obtained with increasing increments of WPC. The results allowed stoichiometric values to be estimated for reactions when using gums at a specific concentration.

Figure 4:
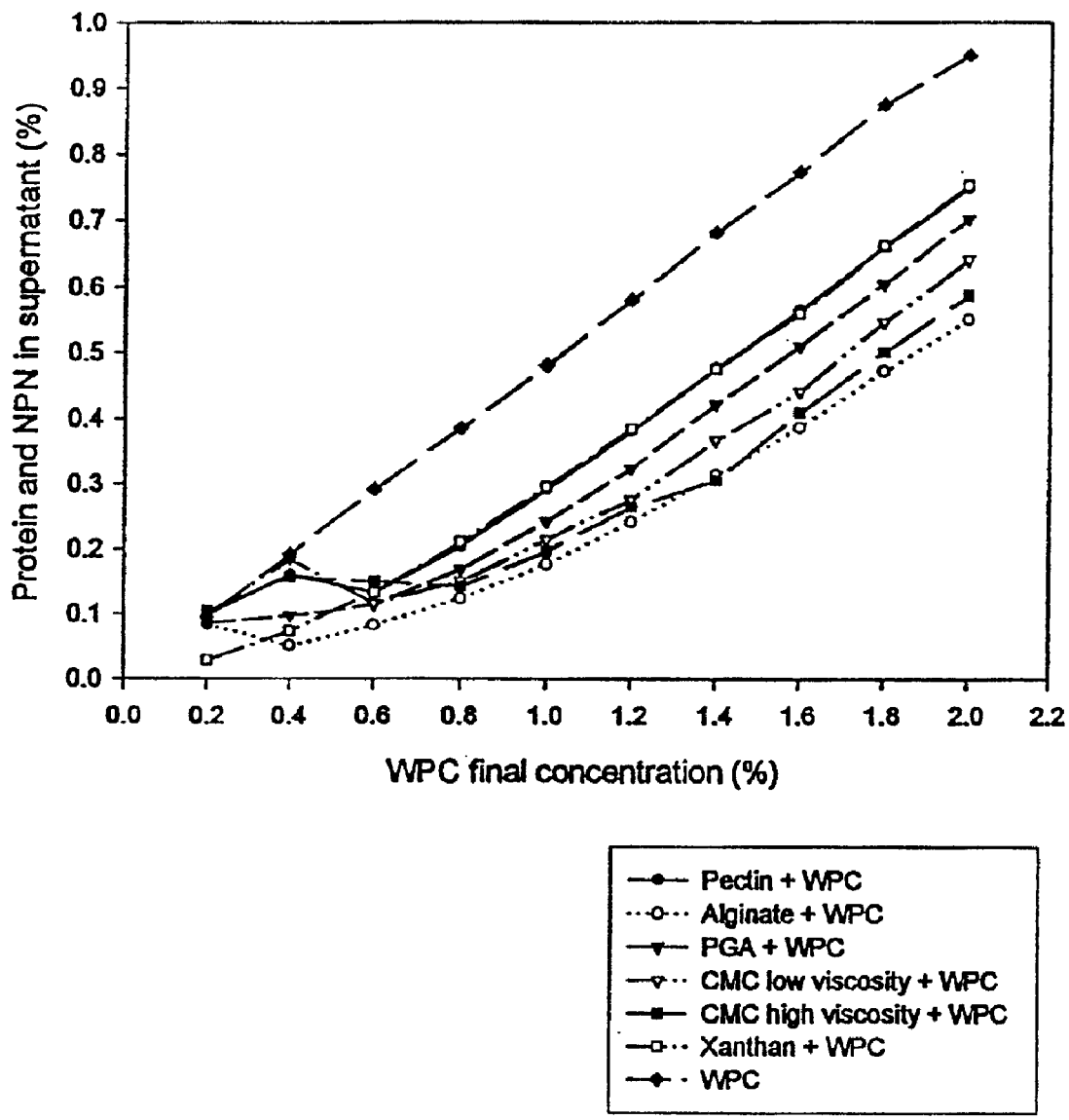
FIG. 4 is a graph showing the protein in the supernatant after reaction of 0.05% polysaccharide solutions with WPC at various concentrations and at pH 4.0.

Stoichiometric values for reactants can be obtained by fixing the concentration of one of the reactants and systematically altering the concentration of the other reactant. Although this design does not account for factor interaction, it does yield an estimate of the required or optimum concentrations for the reagents under specific reaction conditions. FIG. 4 shows the resultant protein and NPN remaining in the supernatant after 0.05% solutions of pectin (●), alginate (○), PGA (▼), low-viscosity CMC (▽), high-viscosity CMC (■) and xanthan gum (□) were reacted with whey proteins from WPC. WPC was added to reach a wide range of final concentration in the mixture and pH was adjusted to 4 prior to centrifugation. A parallel curve, made using centrifuged WPC at the selected concentrations but without added carbohydrates (♦), was analyzed for comparison purposes.

In FIG. 4, the trend of the curves above about 1% WPC concentration is linear and parallel to the protein curve obtained using unreacted WPC. At the lowest final WPC concentration (0.20%), virtually no protein precipitation occurred, except when using xanthan gum at a concentration of 0.05%. The 0.20% WPC was equivalent to roughly 0.10% protein and NPN; this gives a protein (protein+NPN):carbohydrate proportion of 2:1. With about 0.20% protein and NPN concentration (i.e., 0.40% WPC and protein:carbohydrate proportion of 4:1), maximum precipitation of protein complex was reached using alginate. With this same WPC concentration, CMC, both low and high viscosity, resulted in no protein precipitation.

At 0.60% WPC, maximum precipitation was reached using pectin and CMC, low viscosity. The use of PGA resulted in a flat curve without a distinct increase in protein precipitation at a specific pH. However, above 0.60% WPC concentration, the protein curve for the PGA reaction followed a parallel trend to the protein curve. CMC, high viscosity, yielded maximum precipitation of protein only close to 0.80% WPC, resulting in a stoichiometric proportion of 8:1 ((protein+NPN):CMC). These results indicated that optimum concentrations for whey protein precipitation depend on the precipitant used; i.e., to obtain maximum precipitation, independent of fractionation, there will be an optimum proportion of reactants depending on the precipitant.

Figure 5:
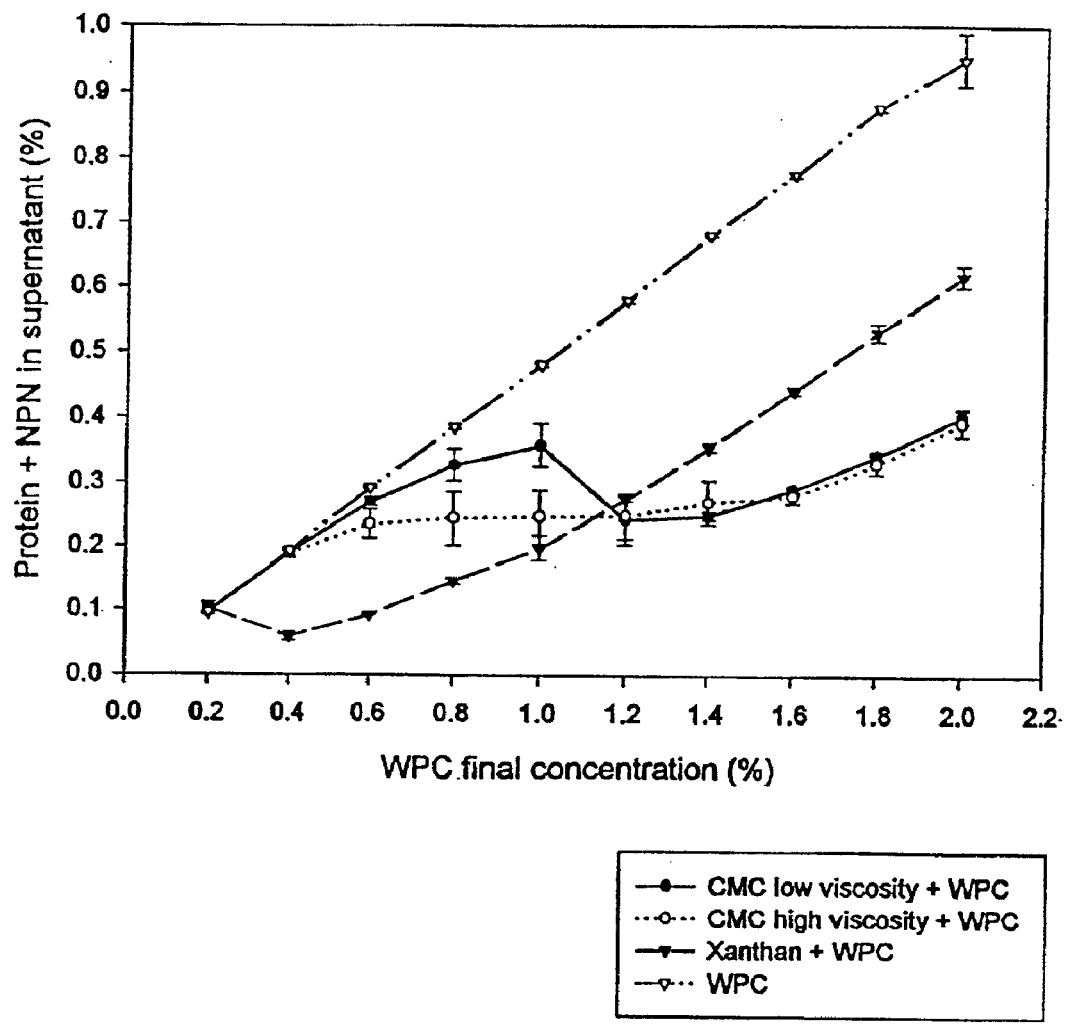
FIG. 5 is a graph showing the protein in the supernatant after reaction of 0.10% polysaccharide solutions with WPC at various concentrations and at pH 4.0.

FIG. 5 shows precipitation of whey proteins by reacting gums at 0.10% concentration with different WPC concentrations and a final pH of 4.0. Xanthan gum (▼), low-viscosity (CMC) (●) and high-viscosity CMC (○) were used in this experiment. Unreacted WPC (▽) is also plotted The same trend observed in FIG. 4 with 0.05% concentration of carbohydrate was observed for reactions using 0.10% carbohydrate. However, at the lowest concentration of WPC, which was 0.20%, xanthan gum did not precipitate whey proteins. Maximum protein precipitation was obtained with 0.40% WPC when 0.10% xanthan gum was used. This concentration corresponded to a protein+NPN:carbohydrate ratio of approximately 2:1. This ratio was similar to the ratio obtained when 0.05% xanthan gum was used. Maximum precipitation of the protein complex using low-viscosity CMC was reached at 1.20 to 1.60% WPC concentration, corresponding to ratio (protein+NPN): CMC of approximately 6:1 to 8:1, respectively. High precipitation of whey protein complex using high-viscosity CMC was reached within a wide range of WPC concentration from 0.60% to 1.60%. This WPC concentration corresponded to a (protein+NPN):CMC ratio of 3:1 to 8:1. In both cases, i.e., with low-viscosity and high-viscosity CMC, the curve of the amount of protein in supernatant was not parallel to the curve of the amount of protein in WPC with no reaction. This suggests that precipitation occurred even at ratios higher than 8:1.

These results show that CMC is a good precipitant when high amounts of protein are present. Using 0.10% low-viscosity CMC, maximum precipitation was reached with WPC:polysaccharide ratio of 12:1 to 16:1. Using high-viscosity CMC, maximum complex precipitation was with a WPC:polysaccharide ratio of 6:1 to 16:1. However, there was no difference in protein precipitation between low- or high-viscosity CMC in the 12:1 to 16:1 ratio of WPC:CMC.

Example 2

Gel Permeation Chromatography of CMC Coacervates Formed at Low Protein Concentration This Example had as an objective to evaluate if the supernatant contained proteins in free form or as soluble complexes after the reaction of gums with a low concentration of WPC. CMC was chosen as the model polysaccharide in the system because the least precipitation occurred when low amounts of WPC were added to it in Example 1.

As shown in Example 1, all but 0.05% xanthan gum failed to precipitate proteins at the lowest WPC concentrations. This was clearly apparent because with low amounts of WPC, when the concentration of protein remaining in the supernatant after reaction with the carbohydrate was equal to the amount of protein in the WPC before reaction. However, it remained unknown if a reaction was really occurring at these low WPC concentrations.

Figure 6:
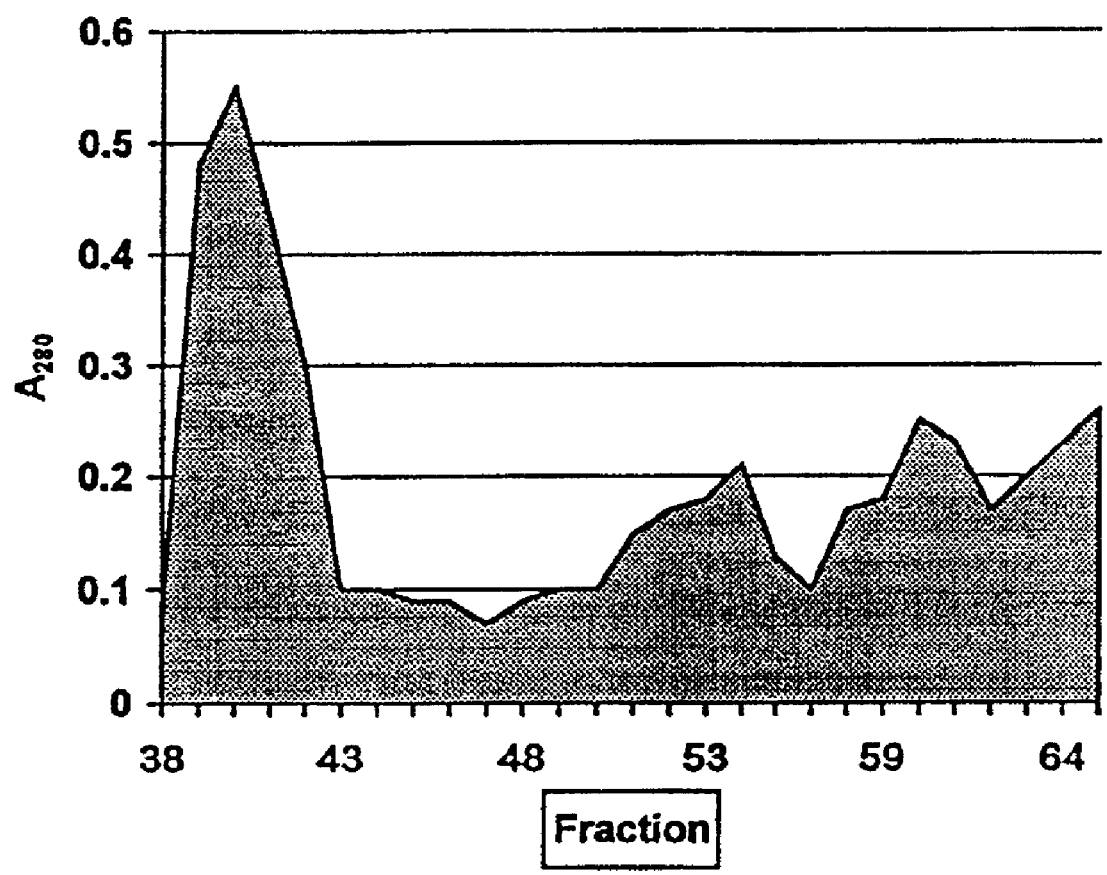
FIG. 6 is a chromatogram of the supernatant after reaction of equal volumes of 0.40% WPC and 0.10% low-viscosity CMC. The first peak from the left corresponds to the whey protein/CMC complex and eluted at the same time as blue dextran, indicating that the complex was eluted in the void volume fraction.

To verify that reaction occurred when there was a low WPC concentration, low-viscosity CMC and high-viscosity CMC, at concentrations of 0.10% were reacted with equal volumes of 0.40% WPC, the mixture was centrifuged at 1200× g for 25 minutes, and the supernatant was analyzed using gel permeation chromatography. Results of the chromatography using low-viscosity CMC are presented in FIG. 6. Similar results were obtained with high-viscosity CMC (results not shown). The first peak that corresponded to the fraction containing whey proteins and carbohydrate (verified by the phenol-sulfuric method). This fraction eluted in the void volume of the column. The range of molecular weight markers used in this experiment was 200,000 to 669,000 Daltons, with Blue Dextran (MW=2,000,000 Daltons) as the indicator of the void volume of the column. Sephadex G-200 has an exclusion limit of about 700,000 Daltons, and the molecular weight of the complexes was higher than this value. These results show that low-viscosity CMC reacts with whey proteins when the WPC has a very small concentration. However, the result is soluble complexes that do not precipitate at the centrifugation conditions used in these Examples. Also, more protein recovery can be obtained if the mixture containing soluble complexes after reaction is processed using membrane microfiltration with a molecular cut-off of approximately 700,000 Daltons.

Because the ratio of protein:CMC in this Example was low, it is possible that the complexes formed were soluble. Complex solubility may be attributed to the high availability of carboxyl groups to bind water, which forms a hydration layer and subsequently results in solubilization. The most likely explanation is that the complexes formed but did not aggregate, and consequently did not precipitate.

Alginate binds to proteins at low pH also. This was confirmed by eluting the alginate-protein complex using gel filtration.

Example 3

Effect of Ionic Strength and Reaction Temperature Over Complex Formation Between Xanthan Gum and Whey Proteins In this Example, the effects of adjusting the ionic strength by adding salts to reconstituted and dialyzed WPC before the reaction with xanthan gum were evaluated at two different temperatures. The objective was to observe if these factors would affect the fractionation of desired proteins. Xanthan gum was chosen because it presented better fractionation results when compared to other gums under the experimental conditions used.

Ionic strength is an important factor in complexation reactions between macromolecules. Ionic strength is a quantity that represents the mean activity coefficient of electrolytes. The definition of ionic strength, I, is:

$$I = \frac{1}{2}\sum m_i z_i^2$$

Where $m_i$ is the molal concentration of ion I, and $z_i$ is its charge. Therefore, when multivalent ions are involved, the ionic strength is greater than the molality.

Figure 7:
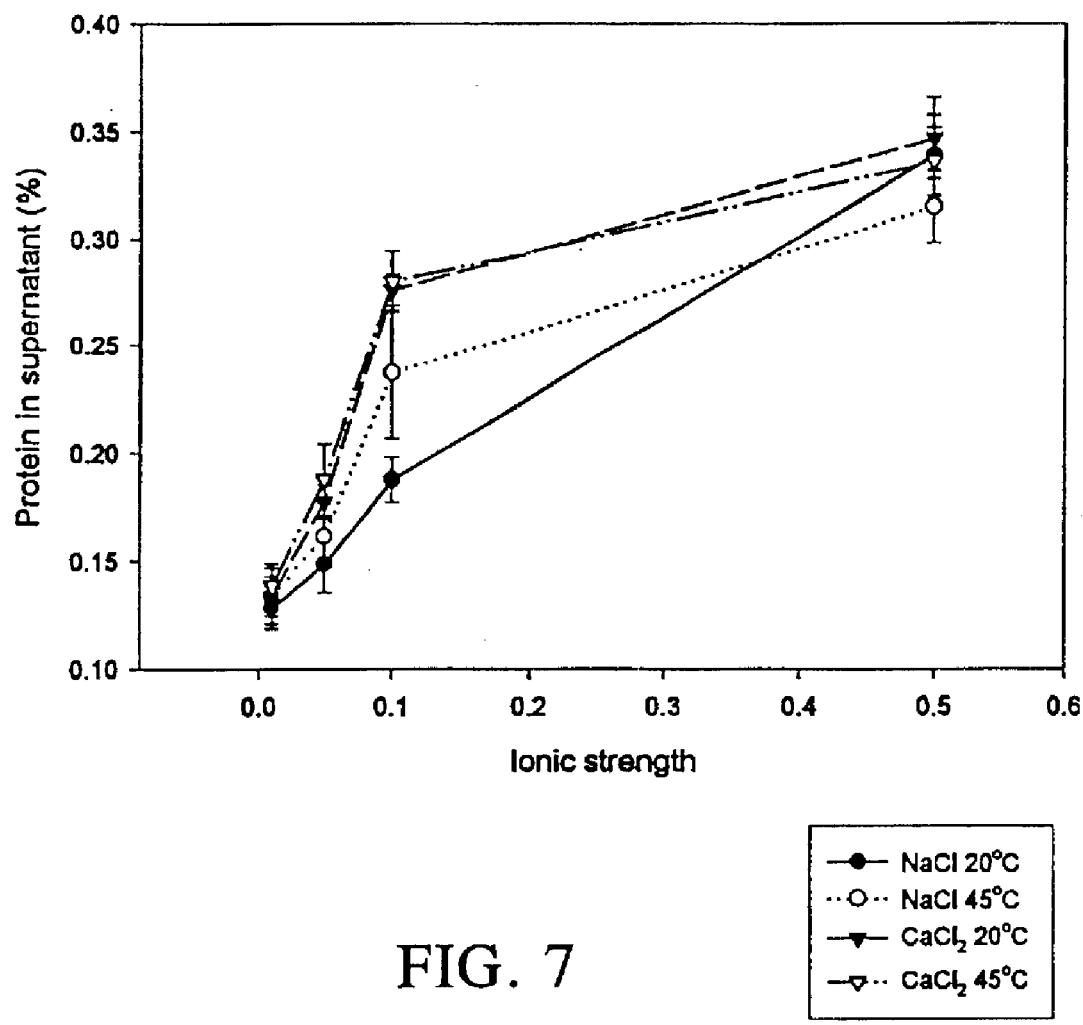
FIG. 7 is a graph showing the protein in the supernatant after reaction of dialyzed 1.4% WPC with 0.10% xanthan gum at 20° C. and 45° C. at anionic strength of 0.01, 0.05, 0.10, and 0.50, using NaCl and $CaCl_2$ (pH 4.5).

Results of this Example are presented in Table 1 and in FIG. 7: NaCl, 20° C. (●); NaCl, 45° C. (○); $CaCl_2$, 20° C.(▼); $CaCl_2$, 45° C.(▽). There was a significant difference in precipitation at different ionic strengths, with less precipitation of whey protein in high ionic strength (P<0.01). At 0.50 ionic strength, no precipitation occurred in the tested treatments. NaCl added to dialyzed WPC to give 0.10 ionic strength at 20°C. (●) resulted in higher precipitation of proteins than the other treatments at this same ionic strength and temperature (P<0.05). No difference was found between the treatments at 0.01 ionic strength. However, high ionic strength treatment using sodium chloride tended to result in more protein precipitation than when calcium chloride was used at the same ionic strength. Temperature of reaction was not significant, except for NaCl at ionic strength of 0.10.

With increasing salt concentration, the ionic strength will increase and this can affect stability of colloid suspensions. For colloidal suspensions, more salt added will result in less stability according to the DLVO (Derjaguin-Landau-Verwey-Overbeek) theory. According to this theory, the double layer repulsion and the van der Waals attractions are added together to produce the overall DLVO pair potential. However, in proteins with added salt, the solubility of protein increases first ("salting in") and then decreases ("salting out"), and this is not predicted by DLVO theory.

TABLE 1

Percentage of whey protein in supernatant after reaction of dialyzed 1.40% WPC with 0.10% Xanthan gum at pH 4.5*, different ionic strength and temperatures*.

| Salt added | Ionic Strength | Temperature (° C.) | Protein in supernatant (%) (± Standard Deviation) |
|---|---|---|---|
| NaCl | 0.01 | 20 | 0.13 ± 0.01$^h$ |
|  | 0.01 | 45 | 0.13 ± 0.01$^h$ |
|  | 0.05 | 20 | 0.15 ± 0.02$^{g,h}$ |
|  | 0.05 | 45 | 0.16 ± 0.02$^{f,g}$ |
|  | 0.10 | 20 | 0.19 ± 0.01$^e$ |
|  | 0.10 | 45 | 0.23 ± 0.03$^d$ |
|  | 0.50 | 20 | 0.34 ± 0.02$^{a,b}$ |
|  | 0.50 | 45 | 0.32 ± 0.02$^b$ |
| CaCl$_2$ | 0.01 | 20 | 0.13 ± 0.02$^h$ |
|  | 0.01 | 45 | 0.14 ± 0.01$^{g,h}$ |
|  | 0.05 | 20 | 0.18 ± 0.01$^{e,f}$ |
|  | 0.05 | 45 | 0.19 ± 0.02$^e$ |
|  | 0.10 | 20 | 0.28 ± 0.01$^c$ |
|  | 0.010 | 45 | 0.28 ± 0.02$^c$ |
|  | 0.50 | 20 | 0.35 ± 0.02$^a$ |
|  | 0.50 | 45 | 0.34 ± 0.02$^{a,b}$ |
| No salt | NA | 20 | 0.12 ± 0.01$^h$ |
|  | NA | 45 | 0.13 ± 0.01$^h$ |

*pH 4.5 of the reactants before mixing
**ionic strength of 0.01, 0.05, 0.10, and 0.50 in the WPC before mixing. Salts used were NaCl and CaCl$_2$
***Temperatures of 20° C. and 45° C.
****Numbers with the same letter in protein % mean equal values (P < 0.05). LSD = 0.021; 5 replicates for each combination of treatment Example 4

Effect of Protein Denaturation Over Complex Formation Between Xanthan Gum and Whey Proteins Protein denaturation due to heat treatment was evaluated in this experiment to verify that it affected the reaction of protein precipitation by xanthan gum.

To test the effect of protein denaturation on the ability of whey proteins to complex using xanthan gum, heat treatment was applied to WPC solutions before reaction. Heating at 90° C. for 30 minutes simulated high heat treatment in the WPC. Also, heating at 121° C. for 15 minutes was attempted, but resulted in high amounts of protein precipitated at different WPC concentrations. Consequently, results of protein precipitation in the WPC solutions heated at 121° C. were overestimated because some of the protein was insoluble before reaction.

Heat denaturation is a factor known to modify functional properties of proteins. Several researchers focused on the effects of heat denaturation of whey proteins, but no investigation has been made to verify the effects of heat denatured whey protein used in the complexation with polysaccharides. The results showed that heating resulted in higher precipitation of whey proteins after reaction with xanthan gum, with less protein in the supernatant. This was observed in some of the treatments. However, there was confusion in the precipitation results, because denaturation affected solubility of proteins, and some precipitation in heated WPC may have been result of protein denaturation and insolubility, rather than only complexation (see Tables 2 and 3).

The extent of denaturation in the WPC samples was measured using a Standard Method based on the modified Harland-Ashworth Method. In this analysis, 20 g of the standards were dissolved in 200 ml of water, giving an initial concentration of approximately 9.00% (wt/wt).

TABLE 2

Undenatured whey protein nitrogen (WPN) in reconstituted WPC after heat treatment.

| Sample | Transmittance (%) | Undenatured WPN (mg/g) ± SD* | Undenatured WPN (m/g) corrected for dilution |
|---|---|---|---|
| WPC 2.00% - not heated | 50 | 7.1 ± 0.1 | 31.9 |
| WPC 1.00% - not heated | 74 | 3.3 ± 0.3 | 29.7 |
| WPC 0.50% - not heated | 85 | 2.0 ± 0.1 | 36.0 |
| WPC 2.00% - 90° C./30 min | 76 | 3.4 ± 0.1 | 15.3 |
| WPC 1.00% 90° C./30 min | 81 | 2.5 ± 0.2 | 22.5 |
| WPC 0.50% 90° C./30 min | 88 | 1.4 ± 0.2 | 27.0 |
| WPC 2.00% 121° C./15 min | 81 | 2.5 ± 0.2 | 11.2 |
| WPC 1.00% 121° C./15 min | 92 | 0.9 ± 0.1 | 8.1 |
| WPC 0.50% 121° C./15 min | 96 | 0.3 ± 0.1 | 5.4 |

*3 replicates for each treatment

TABLE 3

Percentage of whey protein in supernatant after reaction of heat treated WPC* at concentrations of 2.00%, 1.00% and 0.50% with xanthan gum at 0.20%, 0.10% and 0.02% and pH 4.00.

| WPC (%) | Xanthan (%) | Heat (° C.)/ time (min) | Protein in supernatant (% ± Standard Deviation)** |
|---|---|---|---|
| 2.00 | 0.20 | No heating | 0.11 ± 0.006$^a$ |
| 2.00 | 0.20 | 90/30 | 0.09 ± 0.014$^a$ |
| 2.00 | 0.20 | 121/15 | 0.09 ± 0.003$^a$ |
| 2.00 | 0.10 | No heating | 0.16 ± 0.004$^a$ |
| 2.00 | 0.10 | 90/30 | 0.12 ± 0.016$^b$ |
| 2.00 | 0.10 | 121/15 | 0.08 ± 0.002$^c$ |
| 2.00 | 0.02 | No heating | 0.25 ± 0.005$^a$ |
| 2.00 | 0.02 | 90/30 | 0.21 ± 0.003$^b$ |
| 2.00 | 0.02 | 121/15 | 0.11 ± 0.003$^c$ |
| 1.00 | 0.20 | No heating | 0.05 ± 0.003$^b$ |
| 1.00 | 0.20 | 90/30 | 0.04 ± 0.004$^b$ |
| 1.00 | 0.02 | 121/15 | 0.06 ± 0.002$^a$ |
| 1.00 | 0.10 | No heating | 0.05 ± 0.005$^a$ |
| 1.00 | 0.10 | 90/30 | 0.04 ± 0.004$^a$ |
| 1.00 | 0.10 | 121/15 | 0.05 ± 0.006$^a$ |
| 1.00 | 0.02 | No heating | 0.11 ± 0.008$^a$ |
| 1.00 | 0.02 | 90/30 | 0.09 ± 0.006$^b$ |
| 1.00 | 0.02 | 121/15 | 0.05 ± 0.001$^c$ |
| 0.50 | 0.20 | No heating | 0.02 ± 0.000$^a$ |
| 0.50 | 0.20 | 90/30 | 0.03 ± 0.010$^a$ |
| 0.50 | 0.20 | 121/15 | 0.04 ± 0.011$^a$ |
| 0.50 | 0.10 | No heating | 0.02 ± 0.001$^a$ |
| 0.50 | 0.10 | 90/30 | 0.02 ± 0.013$^a$ |
| 0.50 | 0.10 | 121/15 | 0.03 ± 0.005$^a$ |
| 0.50 | 0.02 | No heating | 0.05 ± 0.005$^a$ |
| 0.50 | 0.02 | 90/30 | 0.04 ± 0.003$^a$ |
| 0.50 | 0.02 | 121/15 | 0.03 ± 0.003$^b$ |

*Heat treatments of WPC were 90° C. and 121° C. for 30 min and 15 min, respectively
**Numbers with the same letter in column of protein % mean equal values (P < 0.05) in the same block of treatment, i.e. in the same combination of WP and xanthan concentration, but different heat treatment; 3 replicates were done for each combination of factors.

Because the heated denatured WPC samples were reconstituted and more diluted than the standards, a correction factor for dilution was used. These correction factors were 4.5, 9 and 18 for WPC 2.00%, 1.00% and 0.50%, respectively. The standard curve produced a linear regression equation:

$$Y = 98.1 - 6.69X \text{ and } X = \frac{98.1 - Y}{6.69}$$

Where Y is Transmittance (%) and X is milligrams of undenatured whey protein per gram of dry milk.

The calculated amounts of undenatured whey protein nitrogen in WPC, after correction for dilution factors, were extremely high compared to the standard nonfat dry milk (Table 5). The reason is that whey protein composition in WPC (about 50% protein) is at least 6 to 7 times higher than in nonfat dry milk on a dry basis. As the method detects denaturation in whey protein, results of whey are expected to be higher than results obtained with nonfat dry milk.

Conclusions Drawn from Examples 1–4

Low WPC concentration (about 0.20%) resulted in no precipitation using pectin, alginate, propylene glycol alginate, low- and high-viscosity CMC at 0.05%. Xanthan gum precipitated protein at these concentrations. Using xanthan, low- and high-viscosity CMC at 0.10%, no protein precipitation was reached with 0.20% WPC.

The ratio of protein:carbohydrate affects precipitation of whey protein, with xanthan, pectin, alginate and propylene glycol alginate having the highest protein precipitation in low ranges of protein:carbohydrate ratio. CMC precipitated a high amount of protein only at high protein:carbohydrate ratios.

CMC forms soluble complexes with whey proteins when low protein concentration is present. These complexes have molecular weight of at least 700,000 Daltons.

High ionic strength resulted in less protein precipitation using xanthan gum and WPC, to the point of no precipitation occurring at ionic strength as high as 0.50.

Temperatures of 20° C. and 45° C. did not affect reaction of complexation between xanthan and WPC.

Protein denaturation is not an important factor in the complexation reaction. However, due to aggregation and insolubilization caused by heating, high heat treatments result in more precipitation of proteins, independent of complexation. In practical terms, heat treatments normally used for whey in the dairy industry will not have a significant effect over the denaturation of whey proteins.

The complexes formed by xanthan and whey protein reaction result in fibrous precipitate and are formed by fibers containing groups of thinner fibers held together along a vertical axis.

Example 5

Fractionation of Whey Proteins by Complex Formation

As discussed below, the results obtained in the following Examples show the selectivity of carbohydrate gums in fractionating whey protein under different reaction conditions. Xanthan gum at pH 4.5 and concentration 0.10% showed high selectivity in precipitating certain whey protein when reacting with 1.40% WPC. Specifically, α-lactalbumin remained in the supernatant. In addition, low ionic strength favored the selectivity, i.e., led to an increased proportion of the precipitated protein being β-lactoglobulin.

Based on the results generated in Examples 1–4, a process was devised for whey protein fractionation. In this process, β-lactoglobulin is preferentially precipitated, while α-lactalbumin remains in the supernatant. Diafiltered WPC was reacted with a xanthan gum solution at pH 4.5, resulting in complexation and phase separation. Again, α-lactalbumin remained in the supernatant, while other whey proteins were co-precipitated.

WPC was reconstituted to a concentration of 1.40% total solids and diafiltered in an ultrafiltration unit. Diafiltration was done to adjust the final soluble solids to 10% of initial concentration. Diafiltered WPC at pH 4.5 was reacted with 0.10% xanthan gum at pH 4.5, and, after phase separation, the xanthan/protein complex was precipitated by centrifugation. The supernatant was concentrated by ultrafiltration and freeze-dried. Protein composition in the dry matter of this fraction was 95.5% (wt/wt), and contained 94% α-lactalbumin and 6% β-lactoglobulin. The precipitate, composed of xanthan gum, β-lactoglobulin and other minor proteins, was resolubilized with water and the xanthan/protein complex was split by increasing the pH to 10.0 with 1.0 N sodium hydroxide. After dissolution of the precipitate, isopropanol alcohol was added to precipitate xanthan gum, while β-lactoglobulin and other minor proteins remained in the supernatant. The liquid fraction containing isopropanol was concentrated and diafiltered in an ultrafiltration unit, and freeze-dried. Protein concentration of this fraction was 91.2% of protein in dry matter (wt/wt) with 89% being β-lactoglobulin and 11% being proteins other then α-lactalbumin. Complementary functional properties were obtained with the fractions obtained from WPC. The fraction containing α-lactalbumin had good foaming properties, and the fraction containing β-lactoglobulin presented good emulsification properties.

More specifically, after reaction and separation of the precipitate from the supernatant, the supernatant was concentrated about 20× using an ultrafiltration unit with a polyethersulfone spiral-wound membrane element with a molecular weight cut-off of 10,000 Daltons. The ultrafiltration unit (Alfa Lavel, Pleasant Prairie, Wis.) had a reservoir of 11 liters, and 0.1 liter/min of transmembrane flow with a pump pressure of 1.4 kg/cm². Retentate flow was about 0.5 liter/min at the same pressure. These values were established using water, since other factors modify flow during ultrafiltration of macromolecular solutions. The membrane used had an internal diameter of 1.6 cm, external diameter of 4.5 cm and length of 30.5 cm. The membrane area was about 0.25 m².

Because of low speed, ultrafiltration was performed with unit located inside a walk-in refrigerator to minimize microbial growth. After concentration by ultrafiltration, the retentate was freeze-dried for further analysis.

After reaction and separation, the precipitate was lyophilized, milled, and reconstituted with distilled water to 1.50% (wt/vol) concentration. NaOH at 1.0 N was added to the mixture to reach pH 10.0 and complete dissolution of the precipitate was obtained after agitation. After dissolution, isopropanol alcohol was added in a proportion of 2 parts for each part of the former solution (vol/vol) to precipitate the xanthan gum. KCl was added to the isopropanol before mixing in an amount equivalent to about 2% (wt/wt) of the protein weight in the solution to be precipitated. The objective of KCl addition was to increase the ionic strength. Precipitated xanthan gum was separated by filtration with a stainless steel screen, and analyzed for composition. The remaining liquid phase, which contained β-lactoglobulin and other whey proteins, but entirely lacked α-lactalbumin, was diafiltered in the ultrafiltration unit. After approximately 15-fold concentration, the supernatant was freeze-dried for further analysis.

To measure protein solubility, samples of the protein fractions were reconstituted with distilled water to reach final concentration of about 2.00%, and pH was adjusted to 7.0. One aliquot was centrifuged and the supernatant before and after centrifugation was analyzed for total protein/NPN by the Kjeldahl method.

Example 6

Emulsion Preparation and Analysis

Exactly 25 ml of 2.00% (wt/vol) protein solutions were added to 80 ml of vegetable oil (corn oil, relative density of 0.916 at 25° C.), and mixed for 2 minutes with a Tissumizer Model Ultra Turrox type TP homogenizer, set at 20,000 rpm/min (Tekmar Company, Cincinnati, Ohio).

The stability of the emulsion so formed was evaluated by placing 10 ml of the emulsion into a 20 ml test tube, and allowed to rest undisturbed for 24 hours. After 24 hours, the water content in the bottom 2 ml of the fluid was measured. No change in moisture in this portion was correlated with greatest stability.

The turbidity of the emulsion was then tested. An aliquot (1.0 g) of the emulsion was weighed into a 100 ml volumetric flask, and brought to volume with sodium dodecyl sulfate solution (0.1% wt/vol SDS in distilled water). Of the 1/100 dilution, 1.0 ml was added to 4 ml of 0.1% SDS, for a final dilution of 1/500. Absorbance was determined in this last dilution using a 1-cm wide cuvette, and a BECKMAN®-brand DU-65 spectrophotometer set at 500 nm. If absorbance was higher than 0.8, further dilution was made and a correction factor was allowed in the calculation. See Pearce & Kinsella (1978) *J. Agric. Food Chem* 26:716–723.

$$T = \frac{2.303xa}{b} \text{ where}$$

$T$ = turbidity
$a$ = absorbance(500 nm)
$b$ = path length of cuvette(cm)

The globular size of the droplets was estimated by the formula:

$$R = \frac{3x\phi}{2xT} \text{ Where}$$

$R$ = volume/area mean radius
$\omega$ = oil volume fraction
$T$ = turbidity

Foaming capacity and stability were measured as follows: Solutions (5.0% wt/vol) were whipped using a KITCHEN AID®-brand commercial electric mixer set at speed 8 for 10 minutes (Kitchen Aid Inc., St. Joseph, Mo.). Overrun of the foam was calculated and it was allowed to drain over a period of 30 minutes. Weighing of the drained liquid was made at 5 minute intervals. Results were transformed to categorical values.

The objectives of the above manipulations were to evaluate the basic functional properties of these fractions isolated using the present method.

Results of compositional and functional analyses performed on the fractions obtained are presented in Tables 4, 5, and 6. Xanthan gum was used as the precipitant because, based on previous experiments, it yielded the best results for fractionation among the polysaccharides evaluated. The pH was 4.5 measured before the reaction. Because there is an increase in 0.2 to 0.3 units of pH after complexation, 1.0 N HCl was added to maintain pH 4.5.

The reaction between xanthan gum and whey protein resulted in immediate phase separation with formation of a fibrous precipitate. After separation and concentration by ultrafiltration and drying, the supernatant had about 95.5% (wt/wt in dry matter) of protein with 94% of this protein being α-lactalbumin.

The precipitate was resolubilized with water and the pH increased to 10.0 using sodium hydroxide. This high pH resulted in disruption of the electrostatic interactions between xanthan and whey protein. The amount of precipitate to be resolubilized was not higher than 1.5% (wt/vol), because above this concentration, the solution became extremely viscous. After complex dissolution, isopropanol alcohol was added to precipitate the xanthan gum. α-Lactoglobulin and other minor proteins (except α-lactalbumin) remained in the supernatant, and were concentrated 10 fold by ultrafiltration and diafiltered in two steps using 3 times the volume of the final ultrafiltrate in each of the diafiltration steps. For example, 5 liters of water were used to dissolve 75 g of precipitate, and after precipitate dissolution, 10 liters of isopropyl alcohol were added. Xanthan gum was precipitated, and the mixture of isopropanol/water/protein was concentrated from 15 liters to about 1.5 liters. Then 4.5 liters of water were added, and mixture was ultrafiltered to 1.5 liters. Again, 4.5 liters of water were added, and the mixture ultrafiltered to 1.5 liters.

TABLE 4

Analytical composition of fractions obtained by
reaction of dialyzed 1.40% WPC and 0.10% xanthan gum
at pH 4.5, followed by ultrafiltration.

| Fraction | Moisture (%) ± SD | Ash (%) ± SD | Protein (%) ± SD | Xanthan (%) ± SD |
|---|---|---|---|---|
| Alpha* | 5.90 ± 0.14 | 2.89 ± 0.08 | 89.90 ± 1.67 | 1.31 ± 1.04 |
| Beta** | 7.00 ± 0.56 | 2.46 ± 0.48 | 84.85 ± 1.13 | 5.70 ± 1.13 |
| Xanthan*** | 4.05 ± 0.10 | 2.01 ± 0.05 | 29.47 ± 2.57 | 64.47 ± 2.35 |
| Xanthan/protein Complex | 5.82 ± 0.14 | 0.94 ± 0.04 | 76.80 ± 0.24 | 16.45 ± 0.01 |

*Alpha fraction: supernatant ultrafiltered and freeze-dried
**Xanthan: recovered after dissolution of xanthan/protein complex and precipitation of xanthan by isopropanol alcohol addition.
***Beta fraction: supernatant resulting from isopropanol addition was ultrafiltered, diafiltered and freeze-dried.

TABLE 5

Composition of whey protein in fractions obtained by reaction of dialyzed
1.40% WPC and 0.10% xanthan gum at pH 4.5, followed by
ultrafiltration.

| Fraction | α-lactalbumin (%) | β-lactoglobulin (%) | Other proteins (%) |
|---|---|---|---|
| Alpha* | 94 | 6 | 0 |
| Beta** | 0 | 89 | 11 |

*Alpha fraction: supernatant ultrafiltered and freeze-dried
**Beta fraction: supernatant after isopropanol addition was ultrafiltered, diafiltered and freeze-dried.

TABLE 6

Functionality of fractions obtained from reaction of dialyzed 1.40%
WPC and 0.10% xanthan gum at pH 4.5, followed by ultrafiltration.

| Fraction/Product | Solubility (%) | Globular size | Emulsion stability | Foaming capacity | Foam stability |
|---|---|---|---|---|---|
| WPI | 100 | 2 | ++++ | +++ | +++ |
| WPC | 98 | 2 | ++++ | ++ | + |
| Alpha fraction | 100 | 3 | ++ | ++++ | ++++ |
| Beta fraction | 100 | 1 | ++++ | − | NA |

*Alpha fraction: supernatant ultrafiltered and freeze-dried
**Beta fraction: supernatant after isopropanol addition was ultrafiltered, diafiltered and freeze-dried.
Globular size estimate: 1 = small size (globular size of 0.0 to 0.5); 2 = intermediate (globular size of 0.5 to 1.0); 3 = large (globular size > 1.0)
Emulsion stability: + = unstable; ++++ = highly stable;
Foaming capacity: − = no foaming; + = low foaming capacity (0 to 250% overrun); ++ = intermediate foaming capacity (250 to 500% overrun); +++ = good foaming capacity (500 to 1,000%); ++++ = excellent foaming capacity (more than 1,000% overrun)
Foam stability: + = low stability; ++++ = good stability This was the diafiltration process. After diafiltration, the concentrate was freeze-dried.

The results clearly show the utility of the present invention to fractionate whey proteins in a batch process using xanthan gum and diafiltered WPC.

The "alpha" fraction, which contained α-lactalbumin, had a high protein composition of 90%. Of this amount of protein, 94% was α-lactalbumin, and the remaining 6% was β-lactoglobulin and traces of minor proteins. Ash was equivalent to 2.9%, and a residual amount of 1.3% xanthan gum remained in this fraction.

In contrast, the "beta" fraction was composed of β-lactoglobulin and other minor proteins (immunoglobulins, bovine serum albumin), with a relatively high amount of xanthan gum: 5.70% xanthan remained in the fraction. This means that with the pH increase and the breakage of electrostatic interaction between xanthan and proteins, approximately 75% of the xanthan gum was recovered. This value may be increased if a higher dilution is used. At higher dilution (about 0.8% wt/wt of complex resolubilized in water) a greater amount of xanthan was recovered (up to 85%). This is very beneficial for the economics of the present method because the preferred precipitating agent, xanthan gum, can be recovered from the reaction and used again.

The "beta" fraction had better emulsification properties than the fraction containing α-lactalbumin (Table 6). This was shown by small globule size of the droplets of the emlusion, and the higher emlusion stability.

Once the emulsion was formed, several factors affected stability, and the type of surfactant was one of the most important. Another factor is the uniformity of particle size distribution. If droplet size distribution in an emulsion is not uniform, the small particles tend to disappear and large particles tend to grow larger (i.e., the Ostwald ripening phenomena). In addition, stability is dependent on high viscosity. The residual xanthan gum may have increased the stability of the "beta" fraction by increasing its viscosity.

The fraction containing α-lactalbumin had excellent foaming capacity and foaming stability. In contrast, the fraction containing high amounts of β-lactoglobulin did not foam. Foam is a dispersion of gas in liquid. There is high interfacial tension between the phases in foams, which is shown by the large difference in density across the oil/water interface. Because the pressure difference at the interface of foam is larger than that in an emulsion, foam is less stable than an emulsion.

The results of this Example show that complementary functional properties were obtained with the fractions obtained from WPC. The fraction containing α-lactalbumin had good foaming properties, and the fraction containing β-lactoglobulin presented good emulsification properties.

Several conclusions can be drawn from this Example:

Complex formation with reaction of xanthan gum and whey proteins, followed by ultrafiltration, resulted in fractionation of whey proteins.

After reaction of xanthan gum and WPC, the supernatant was processed and results showed that 94% of the protein in this fraction was α-lactalbumin.

After processing of the precipitate, at least 75% of xanthan was recovered, and a fraction containing 89% β-lactoglobulin and 11% proteins other than α-lactalbumin was obtained.

The fractions obtained had complementary functional properties. The fraction containing α-lactalbumin had good foaming properties, and the fraction containing β-lactoglobulin yielded good emulsification properties.

What is claimed is:

1. A method of fractionating α-lactalbumin from β-lactoglobulin in whey or whey protein concentrate comprising:
    (a) contacting whey or whey protein concentrate with a complexing agent wherein the complexing agent forms insoluble complexes with β-lactoglobulin present in the whey or whey protein concentrate; and then
    (b) separating the insoluble complexes from the whey or whey protein concentrate thereby yielding a precipitate that comprises at least 95% β-lactoglobulin, and a supernatant that comprises at least 95% α-lactalbumin.

2. The method of claim 1, further comprising after step (b), step (c): concentrating the α-lactalbumin present in the supernatant.

3. The method of claim 1, further comprising after step (b), step (c): disassociating the insoluble complexes contained within the precipitate.

4. The method of claim 3, wherein the precipitate is treated with an alcohol to disassociate the complexes.

5. The method of claim 3, wherein the precipitate is treated with a $C_1$ to $C_6$ alcohol to disassociate the complexes.

6. The method of claim 3, wherein the precipitate is treated with isopropyl alcohol to disassociate the complexes.

7. The method of claim 3, further comprising after step (c), step (d): isolating β-lactoglobulin from the disassociated complexes.

8. The method of claim 1, wherein the complexing agent is selected from the group consisting of pectin, sodium alginate, propylene glycol alginate, carboxymethylcellulose, and xanthan gum.

9. The method of claim 8, wherein the complexing agent is pectin.

10. The method of claim 8, wherein the complexing agent is sodium alginate.

11. The method of claim 8, wherein the complexing agent is propylene glycol alginate.

12. The method of claim 8, wherein the complexing agent is carboxymethylcellulose.

13. The method of claim 8, wherein the complexing agent is xanthan gum.

14. The method of claim 1, wherein in step (a), the whey or whey protein concentrate is contacted with the complexing agent in an aqueous solution of about pH 4.0.

15. The method of claim 1, wherein in step (a), the concentration of the whey, or whey protein concentrate, in an aqueous solution is no less than about 0.20% wt/vol.

16. The method of claim 1, wherein in step (a), the concentration of the complexing agent in an aqueous solution is no less than about 0.05% wt/vol of the complexing agent.

17. The method of claim 1, wherein in step (a), the whey or whey protein concentrate is contacted with the complexing agent in a solution having an ionic strength of from about 0.01 to about 0.50.

18. A method of fractionating α-lactalbumin from β-lactoglobulin in whey or whey protein concentrate comprising:
(a) contacting whey or whey protein concentrate with a complexing agent selected from the group consisting of pectin, sodium alginate, propylene glycol alginate, carboxymethylcellulose, and xanthan gum, wherein the complexing agent forms insoluble complexes with β-lactoglobulin present in the whey or whey protein concentrate; and then
(b) separating the insoluble complexes from the whey or whey protein concentrate thereby yielding a precipitate that comprises at least 95% β-lactoglobulin, and a supernatant that comprises at least 95% α-lactalbumin.

19. The method of claim 18, further comprising after step (b), step c): concentrating the α-lactalbumin present in the supernatant.

20. The method of claim 18, further comprising after step (b), step c): disassociating the insoluble complexes contained within the precipitate.

21. The method of claim 20, wherein the precipitate is treated with an alcohol to disassociate the complexes.

22. The method of claim 21, wherein the precipitate is treated with a $C_1$ to $C_6$ alcohol to disassociate the complexes.

23. The method of claim 21, wherein the precipitate is treated with isopropyl alcohol to disassociate the complexes.

24. The method of claim 21, further comprising after step (c), step (d): isolating β-lactoglobulin from the disassociated complexes.

25. The method of claim 18, wherein in step (a), the whey or whey protein concentrate is contacted with the complexing agent in an aqueous solution of about pH 4.0.

26. The method of claim 18, wherein in step (a), the concentration of the whey, or whey protein concentrate, in an aqueous solution is no less than about 0.20% wt/vol.

27. The method of claim 18, wherein in step (a), the concentration of the complexing agent in an aqueous solution is no less than about 0.05% wt/vol.

28. The method of claim 18, wherein in step (a), the whey or whey protein concentrate is contacted with the complexing agent in a solution having an ionic strength of from about 0.01 to about 0.50.

29. A method of fractionating α-lactalbumin from β-lactoglobulin in whey or whey protein concentrate comprising:
(a) contacting whey or whey protein concentrate with xanthan gum in an aqueous solution having an ionic strength of from about 0.01 to about 0.5, whereby the xanthan gum forms insoluble complexes with β-lactoglobulin present in the whey or whey protein concentrate; and then
(b) separating the insoluble complexes from the whey or whey protein concentrate thereby yielding a precipitate that comprises at least 95% β-lactoglobulin, and a supernatant that comprises at least 95% α-lactalbumin.

30. The method of claim 29, further comprising after step (b), step (c): concentrating the α-lactalbumin present in the supernatant.

31. The method of claim 29, further comprising after step (b), step (c): disassociating the insoluble complexes contained within the precipitate.

32. The method of claim 31, wherein the precipitate is treated with an alcohol to disassociate the complexes.

33. The method of claim 32, wherein the precipitate is treated with a $C_1$ to $C_6$ alcohol to disassociate the complexes.

34. The method of claim 32, wherein the precipitate is treated with isopropyl alcohol to disassociate the complexes.

35. The method of claim 29, further comprising after step (c), step (d): isolating β-lactoglobulin from the disassociated complexes.

36. The method of claim 29, wherein in step (a), the whey or whey protein concentrate is contacted with the complexing agent in an aqueous solution of about pH 4.0.

37. The method of claim 29, wherein in step (a), the concentration of the whey, or whey protein concentrate, in an aqueous solution is no less than about 0.20% wt/vol.

38. The method of claim 29, wherein in step (a), the concentration of the complexing agent in an aqueous solution is no less than about 0.05% wt/vol.

* * * * *